United States Patent [19]

Peterlik et al.

[11] Patent Number: 4,921,697
[45] Date of Patent: May 1, 1990

[54] IFN-GAMMA AS AN ACTIVE SUBSTANCE FOR INHIBITING AND PREVENTING DEGRADATION PROCESSES IN BONE

[75] Inventors: Meinrad Peterlik; Oskar Hoffmann, both of Vienna, Austria

[73] Assignee: Boehringer Ingelheim International GmbH, Ingelheim am Rhein, Fed. Rep. of Germany

[21] Appl. No.: 868,524

[22] Filed: May 30, 1986

[30] Foreign Application Priority Data

May 30, 1985 [DE] Fed. Rep. of Germany ....... 3519361

[51] Int. Cl.$^5$ ...................... A61K 45/02; C07K 15/26
[52] U.S. Cl. .................. 424/85.5; 424/85.4; 530/351
[58] Field of Search ............................... 424/85, 85.5

[56] References Cited

FOREIGN PATENT DOCUMENTS 3436638 4/1986 Fed. Rep. of Germany .

OTHER PUBLICATIONS

Kayander et al., The Lancet, vol. I, pp. 984–985, 1979.
Butler et al., The Lancet, vol. II, pp. 278–279, 1984.
Takahashi et al., J. Immunol., vol. 137, pp. 3544–3549, 1986.
Peterlik et al., *FEBS Lett.*, 185:287–290 (1985).
Gowen, M., *J. Immunol.*, 136:2478–2481 (1986).
Stephenson, M. L. et al., *FEBS Lett.*, 180:43–50 (1985).
Jilka, R. L. et al., *Biochem. Biophys. Res. Comm.*, 120:553–558 (1984).
Nilsson, O. S. et al., *J. Interferon Res.*, 4:135–140 (1984).

*Primary Examiner*—Blondel Hazel
*Attorney, Agent, or Firm*—Saidman, Sterne, Kessler & Goldstein

[57] ABSTRACT

This invention relates to methods for preventing and treating bone diseases caused by bone loss comprising administering to a patient a pharmaceutical composition with IFN-γ as the active substance.

11 Claims, 8 Drawing Sheets

IFN-GAMMA AS AN ACTIVE SUBSTANCE FOR INHIBITING AND PREVENTING DEGRADATION PROCESSES IN BONE

FIELD OF THE INVENTION

The present invention relates to methods for preventing and treating bone diseases caused by bone loss comprising administering to a patient a phamarmaceutical composition with IFN-γ as the active substance.

BACKGROUND OF THE INVENTION

Living bone tissue is subject to a constant rebuilding process in which new bone formation and decomposition are in equilibrium under physiological conditions. The new formation of mineralized bone (bone formation) is determined essentially by the activity of the osteoblasts. The function of these mesenchymal cells is the synthesis and secretion of the individual components of the organic bone matrix, mainly collagen type T, that is then mineralized by the deposition of hydroxyl apatite. The decomposition of mineralized bone is effected by osteoclasts e.g., polynuclear giant cells which are probably formed by cell fusion from monocytes (macrophages). Baron, et al., "Lymphocytes, Macrophages and the Regulation of Bone Remodeling," in: *Bone and Mineral Research, Annual* 2 (W.A. Peck, ed.), p. 175, (Elsevier 1983).

The activity of the osteoblasts and osteoclasts is coordinated under physiological conditions by a complex regulating mechanism which maintains the dynamic equilibrium between the processes of formation and decomposition. Regulation is effected not only by the hormones 1,25-dihydroxy vitamin $D_3$, parathormone and calcitonin (Raisz et al., "Hormonal Control of Skeletal Growth, *Ann. Rev. Physiol.*, 43:225 (1981)) but also by various local mediators and tissue hormones (G.L. Wong, "Paracrine Interactions in Bone-Secreted Products of Osteoblasts Permit Osteoclasts to Respond to Parathyroid Hormone," *J Biol. Chem.*, 259:4019–4022 (1984)) particularly prostaglandins ((Raisz et al., supra) and as yet unidentified "coupling factors" (Howard et al., "Parathyroid Hormones Stimulates Bone Formation and Resorption in Organ Culture: Evidence For a Coupling Mechanism," *Proc. Natl. Acad. Sci. USA*, 78:3204–3208 (1981)).

The "coupling factors" have been held to be responsible for the increased activity of the osteoblasts after stimulation of the osteoclast activity. This phenomenum indicates that increased decomposition may be compensated by increased bone formation. Disorders of this equilibrium may result in numerous osteopathies, and one in particular, osteoporosis, one of the most frequent bone diseases. With osteoporosis, there is a loss of bone mass i.e. the mineralized content and the organic bone matrix, chiefly at an advanced age. This bone loss from osteoporosis is far greater than what would be expected for that age.

In particular, women after menopause are affected by osteoporosis. Thus, for example, tests in the USA have shown that 25% of all women over 65 suffer from this disease. L.V. Avioli, "Osteoporosis," in: *Bone and Mineral Research, Annual* 1 (W.A. Peck, ed.) p. 280–318, (Elsevier 1983). Approximately 3 to 4 million are affected in the Federal Republic of Germany. The consequence of bone loss is an increased number of bone fractures, e.g. the spine, the neck, the femur or the wrist, i.e. parts of the body which are subjected to particularly great stresses. These fractures often cause severe and lasting restrictions of movement and disabilities. A typical change is the curvature of the spinal column, affecting the mobility of the patient. However, in addition to causing constant pain, the bent posture also affects the heart and lungs and the gastrointestinal tract.

The calcium levels and various hormones which control the calcium level and hence also the mineralization of the bone and the new formation of the organic bone matrix are particularly implicated in this disease. The oestrogens which decrease in women at menopause are of particular importance in this respect.

With regard to the specific activities of the individual hormones and mediators, it is clearly established that parathormone and vitamin D, and particularly the metabolite thereof, 1,25-dihydroxy vitamin $D_3$, formed in the kidneys, primarily inhibit the osteoblast activity. Rodan et al., "Role of Osteoblasts in Hormonal Control of Bone Resorption—A Hypothesis," *Calcif. Tissue Int.*, 33:349–351 (1981). In addition, these hormones and mediators seem to facilitate the fusion of monocyte-like precursors and thus contribute to an increase in the number of osteoclasts in the bone tissue. Feldman et. al., "Effects of Parathyroid Hormone and Calcitonin on Osteoclast Formation in Vitro," *Endocrinology*, 107:1137–1143 (1980). Prostaglandins also, by means of a different mechanism, bring about an increase in the number and activity of osteoclasts. Shelling et al., "Role of the Osteoclast in Prostagladin $E_2$-Stimulated Bone Resorption," *Lab. Invest*, 42:290–295 (1980).

Recently it has been found that interleukins and lymphokines may also play a specific role in the process of bore rebuilding (Baron et al., supra). Interleukin 1, which is formed within the framework of the immune response of macrophages, accelerates the decomposition of bones in organ culture, part of its activity being based on the fact that the endogenic synthesis of osteolytically active prostaglandins is stimulated. Beresford et al., "The effects of Monocyte-Conditioned Medium and Interleukin 1 on the Synthesis of Collagenous and Non-Collagenous Proteins by Mouse Bone and Human Bone Cells in Vitro," *Biochim. Biophys. Acta*, 801:58–65 (1984). The so-called "osteoclast activiating factor" (OAF) also has an osteolytic activity imparted by prostaglandins. Bockman et al., "Lymphokine-Mediated Bone Resorption Requires Endogenous Prostaglandin Synthesis," *J. Exp. Med.*, 154:529–534 (1981).

The treatment of osteoporosis is difficult since at present the loss of bone substance is virtually impossible to reverse. Treatments such as rebuilding the bone mass by means of fluorides is contentious. The aim of therapy must therefore be to prevent the progress of the disease by reducing the bone decomposition processes to the extent of new bone formation.

It is also important to prevent the disease. In the USA, women are advised to take sufficient calcium with their food and to do so even before menopause.

It has been known for some time that calcitonin, a peptide hormone, can also inhibit bone decomposition. In particular, calcitonin inhibits the effect of parathormone on the osteoclasts. In addition, calcitonin also appears to have its own suppressant effect on osteoclast activity. (Raisz et al., supra.) However, calcitonin treatment is laborious and is recommended only for patients in whom bone loss is already well advanced. Furthermore, this treatment is advisable only for limited periods since its affect is only temporary due to an "escape" phenomenon.

It would be desirable, therefore, to have a method of treating and for preventing and inhibiting bone disease caused by bone loss.

SUMMARY OF THE INVENTION

The aim of the present invention was therefore to provide for a method for treating diseases of the skeleton caused by bone loss.

Surprisingly, the inventors have found that gamma-interferon (IFN-γ) has an extremely powerful regulating effect on the processes occurring during bone formation and decomposition.

The invention relates to the use of IFN-γ in methods for regulating the effect on the processes which occur during bone formation and decomposition.

DETAILED DESCRIPTION OF THE INVENTION

Gamma-interferon (IFN-γ), also known as immune interferon, is, like interleukin 1, regarded as a lymphokine since it is formed on lymphocytes after either specific or non-specific stimulation by antigens to which the lymphocytes have previously been sensitized. It was assumed that IFN-γ could promote the fusion of monocytes in osteoclasts since it had been found that IFN-γ in a culture of human blood monocytes promotes the formation of polynuclear giant cells (polykaryones). Weinberg, et al., "Recombinant Human γ-Interferon Induces Human Monocyte Polykaryon Formation," *Proc. Natl. Acad. Sci. USA*, 81:4554-4557 (1984). Furthermore, IFN-γ is able to activate macrophages and these macrophages may then develop osteolytic activities.

Thus, one skilled in the art would have expected gamma-interferon to promote the decomposition of demineralized bone brought about by osteoclasts. The inhibiting effect on the osteolytic mechanisms is therefore all the more surprising.

The present invention describes, for the first time, that IFN-γ is capable of inhibiting processes which lead to pathological bone loss. This is achieved primarily by suppression of the endogenic synthesis of osteolytically active prostaglandins in the bone by interaction of gamma-interferon with the prostaglandin synthetase complex (cyclooxygenase system). Calcitonin does not have this effect.

This inhibition of prostaglandin synthesis in the bone is an effect specific to IFN-γ. No such effect has been demonstrated for either IFN-α,β. (See examples). A second effect, similar to that of calcitonin, shown by IFN-γ is the inhibition of the osteoclast activity stimulated by parathormone. However, this effect of IFN-γ can only be detected at higher concentrations. This calcitonin-like activity appears to be exerted by other types of interferon as well, since Jilka and Hamilton for example, have shown that human leucocyte interferon is capable of inhibiting PTH-induced bone resorption in organ culture. Jilka et al., "Inhibition of Parathormone Stimulated Bone Resorption by Type 1 Interferon," *Biochem. Biophys. Res. Comm.*, 120:553-558 (1984).

The inhibition of prostaglandin synthesis by gamma-interferon is surprising since one skilled in the art would assume that interferons would be more likely to stimulate prostaglandin synthesis. Stringfellow et al., "Interferons and Prostaglandins," in: *Interferon, vol.* 2 (J. Vilcek and E. De Maeyer, eds.), p. 147-163, (Elsevier 1984). For example, the fever occurring during therapy with alpha- and betainterferons has been attributed to an increase in the PGE$_2$ concentration in the hypothalamus, Dinarello et al., "Mechanisms of Fever Induced by Recombinant Human Interferon," *J. Clin. Invest.* 74:906-913 (1984).

The explanation for this surprising effect of gamma-interferon on osteolysis rests in a particular specificity of the cyclooxygenase system of bone. Differences in tissue specificity of the prostaglandin synthetase complex have long been known. R.J. Flowers, "Drugs Which Inhibit Prostaglandin Biosynthesis," *Pharmacol. Rev.*, 26:33-67 (1974). In bone, this enzyme complex does not appear to be sensitive to IFN-α and IFN-β. Apart from results already obtained (see Example 4) this would also appear to be shown by the fact that, in the study by Jilka and Hamilton, mentioned above, type I interferon was not found to have any influence whatever on basal bone resorption. Another indication of the differing sensitivity of the enzyme complex can be found in the tests by Nilsson et al. in which the effect of mouse interferon from C-243 cells on heterotopic bone implants in mice was investigated. Nilsson et al., "Effect of Interferon on Heterotopic New Bone Formation in Mice," *J. Interferon Res.*, 4:135-140 (1984). No indications of any osteolytic activity of this interferon were obtain in this research. Osteolytic activity of interferon would be expected if the interferon was used to stimulate prostaglandin synthesis in the bone as well as in the hypothalamus.

A further object of the invention is the use of gamma-interferon as an active substance in a pharmaceutical composition for treating diseases caused by pathologically altered, local or generalized bone decomposition, such as osteoporosis.

The etiology and pathogenesis of senile osteoporosis are largely unclear but it is widely accepted that a relative predominance of degradative processes leads to a pathological rarification of the bone mass. It is striking that patients with osteoporosis do not show any significant changes with regard to the serum levels of the bone-resorbant hormones PTH and 1,25dihydroxy vitamin $D_3$. It is therefore assumed that the increased rate of bone decomposition can be traced primarily to the effect of local factors. Indications of this can be found in a study by Atik et al. who found a higher $PGE_2$ activity in bone biopsies on patients with senile osteoporosis than in control persons. Atik et al., "Prostaglandin $E_2$-Like Activity and Senile Osteoporosis," *Prostaglandins Leukotrienes Med.*, 11:105–107 (1983). Fujik et al. discovered, in patients with osteoporosis, a change in the ratio of T-helper to T-suppressor lymphocytes and concluded that a disturbed immune regulation might be possible in osteoporosis. (Fujik et al., "T Lymphocyte Subsets in Osteoporosis, Effect of 1-Alpha-Hydroxyvitamin $D_3$, "*Mineral Electrolyte Metab.*, 10:375–378 (1984)). This conclusion is of importance insofar as the very immune-regulating factors interleukin 1 and osteoclastic activating factor are stimulators of PG synthesis.

The surprising inhibitory effect of IFN-$\gamma$ on PG synthesis in bone presents particular advantages in the treatment of osteoporosis since IFN-$\gamma$ influences bone resorption in a manner similar to the way calcitonin works. This hormone has been shown to have good effects in osteoporosis therapy. (Round Table Discussion: Pathogenesis and Treatment of Postmenopausal Osteoporsis. *Calcif. Tissue Int.*, 35:708–711 (1983)). As already stated, however, calcitonin has no effect on PG synthesis as its mechanism of activity is difference from IFN-$\gamma$. These differences give rise to methods of using both IFN-$\gamma$ and calcitonin together to treat bone disease, and of using IFN-$\gamma$ and calcitonin in combination to treat bone disease.

The surprising inhibition of prostaglandin synthesis by IFN-$\gamma$ makes it the counterpart of interleukin 1 and the osteoclast activating factor (OAF) in the process of bone rebuilding. This property is therapeutically important since the osteolytic activity of prostaglandins, the synthesis of which is stimulated by various inflammation mediators, including OAF, in diseases of the rheumatic type, particularly in rheumatoid arthritis and similar diseases, contributes to the destruction of the joints observed in this disease. The present invention therefore also relates to the use of IFN-$\gamma$ according to the invention of the treatment of rheumatic type diseases, particularly rheumatoid arthritis.

Corresponding therapy with IFN-$\gamma$ is particularly advantageous compared with treatment with nonsteroidal anti-inflammatory substances (e.g. indomethacin), since these very substances have severe side effects (acute ulcers) owing to their inhibitory effect on PG synthesis in other tissues as well (e.g. the mucous membrane of the stomach). However, many non-steroidal anti-phlogistic agents have only a slight inhibitory effect on PG synthesis. A combination of these agents with IFN-$\gamma$ according to this invention is advantageous due to IFN-$\gamma$ selective effect on PG synthesis in the bone.

Depending on the dosage used, IFN-$\gamma$ may have both an inhibitory and a stimulating effect on the production of immunoglobulins by B-lymphocytes. In various immune diseases, interferons have actually been found in patients' sera. However, these IFN activities should be ascribed to a changed IFN-$\gamma$ rather than to an IFN-$\gamma$. As for immunity provided by the cells, IFN-$\gamma$ generally has an inhibiting effect on the proliferation of T-lymphocytes and can thus suppress phenomena of cell-borne immunity such as transplant rejection or hypersensitity reactions of the delayed type, which would be advantageous in the treatment of PCP. On the other hand, IFN-$\gamma$ may cause stimulation of the cell's immune response under certain conditions. (Friedman et al., "Interferons with Special Emphasis on the Immune System," in: *Advances in Immunoloqy*, vol. 34 (F.J. Dixon and H.G. Kunkel, eds.), p. 97–140, Academic Press (New York 1983)). Therefore IFN-$\gamma$ may be used according to this invention in a method for treating a primarily chronic polyarthritis, such as rheumatoid arthritis, a disease involving a variety of autoimmune phenomena.

In addition to suppressing tumor growth, the ability of IFN-$\gamma$ to suppress prostagladin synthesis in the bone according to this invention is advantageous in the treatment of tumors that contribute to metastasis in the bones and to bone decomposition. These tumors produce prostaglandins or stimulate prostaglandin synthesis in the bone. (Warner et al., "Ametantrone Inhibits Prostaglandin-Mediated Resorption in Bone Organ Culture," *Prostaglandins*, 28:469–476 (1984)).

The demonstrated effect of gamma-interferon on processes occurring during bone formation and decomposition thus, surprisingly, makes gamma-interferon an outstanding active substance for the preparation of pharmaceutical compositions for use in the treatment of systemic or local bone diseases with an inflammatory or non- inflammatory genesis (degenerative diseases), which may be caused by inhibition of bone formation or by increased resorption of the bone.

These bone diseases include, in addition to those already mentioned, various osteodystrophies caused by parathormone, particularly renally induced osteopathies. Bone resorption caused by parathormone in progressive kidney failure is known. In some of these diseases, glomerulonephritides caused by the autoimmune system are observed. In precisely these cases, IFN-$\gamma$ is exceptionally well suited as a therapeutical active substance with immune-suppressant properties. The methods using IFN-$\gamma$ as an active substance according to the invention inhibits bone resorption and effectively influences the autoimmune reaction.

Similarly, another osteodystrophy, Paget's disease can be treated with the agent according to the invention.

Furthermore, IFN-$\gamma$ has the advantage of being suitable for use in all cases in which there is a lack of response and/or immune reactions in the course of calcitonin therapy.

The use of IFN-$\gamma$ according to the invention may be combined as previously mentioned, with calcitonin or with other agents known for the treatment of bone diseases.

The use of IFN-$\gamma$ according to the invention is also extremely suitable for treating jaw and bone diseases with increased bone loss such as, for example, alveolar bone resorption, generally referred to as periodontal diseases, which often occur even in the young patients. The use of IFN-$\gamma$ according to the invention may be administered to the human patient or mammals to be treated systemically or locally, for example, by intra-articular injection, oral, topical, parenteral and buccal administration. All the forms for administration which bring about an increase in the gamma-interferon plasma/tissue level are suitable, for example the solutions conventionally administered for IFN-γ. However, other dosage forms are also possible.

Small amounts of IFN-γ are sufficient for the use according to the invention. The dosage and dosage rate may be similar to those currently applied to IFN-γ in clinical trials. The dosage may be varied depending on the site of administration. The critical factor is that the dosage must be selected so as to achieve an effective increase in the gamma-interferon plasma/tissue level. For example, for treating a bone disease IFN-γ may be administered such that patients receive from about one quarter milliliter to about one milliliter, preferably from about one quarter milliliter to about one half milliliter. Dosages for preventing bone disease may be less than for treating such disease.

The pharmaceutical compositions containing the IFN-γ according to the invention may contain conventional pharmaceutical excipients and/or vehicles and/or stabilizers. Examples of suitable stabilizers include amino acids, di-, tri- and tetrapeptides, sugars or albumins. One skilled in the art will be aware of a plurality of excipients, vehicles and stabilizers and will be able to formulate them with the IFN-γ according to the invention without undue experimentation. These substances and formulations are described by E.W. Martin in *Reminqton's Pharmaceutical Sciences*.

The following examples are intended to illustrate the invention more fully without limiting the invention in any manner.

EXPERIMENTS

The specific activity of recombinant mouse IFN-γ (from *E.coli*) (Ernst Boehringer Institute fur Arzneimittelforschung, Vienna) was $1.3 \times 10^7$ antiviral units per mg. IFN-γ was dissolved in RPMI medium and stored in a deep frozen state until required. IFN-γ, (from Ehrlich ascites cells, induces with Newcastle Disease virus, superinduced with theophyllin, was a product of Enzo Biochem, Inc. (N.Y.), (Ernst Boehringer Insitute fur Arzneimittelforschung). The specific activity of batch no. 3-07001 was $44 \times 10^6$ U/mg of protein. The activity of the solution used was determined to be 60,000 units per ml. The synthetic salmon-calcitonin used for comparison purposes (specific activity 100 MRC units/ml) was a product of Sanabo (Vienna). Parathormone was used as the synthetic N-terminal fragment 1-34 of Bachem, Torrance, Calif. The prostaglandin $E_2$ was a product made by Upjohn under the name prostin $E_2$. Bovine thrombin is a specialty of Hoffman-LaRoche (topostasin) while the indomethacin used was produced by Merck, Sharp and Dohme.

Neonatal mouse calvaries may be kept in organ culture for fairly long periods (up to 96 hours or more). Experimental details have been described by various authors. (Shelling et al., "Role of the Osteoclast in Prostaglandin $E_2$-Stimulated Bone Resorption," *Lab. Invest.*, 42:290-295 (1980); Krieger et al., "Interaction Between Amrinone and Parathyroid Hormone on Bone in Culture," *Am. J. Physiol.*, 243:E499-504 (1982); Stern et al., "Comparison of Fetal Rat Limb Bones and Neonatal Mouse Calvaria: Effects of Parathyroid Hormone and 1,25-Dihydroxyvitamin $D_3$," *Calif. Tissue Int.*, 35:172-176 (1983)). The particular mice used were SPF mice 4 to 6 days old (Institute fur Versuchstierzucht of Vienna University, Himberg). The strain designation was HIM:OF.

The calvaries were prepared under sterile conditions (laminar flow). After the connective tissue adhering to them has been carefully removed the bones were transferred into 1.0 ml culture medium (see below) in test tubes. After treatment with 50% $O_2$, 45% $N_2$ and 5% $CO_2$, these test tubes were firmly sealed and then incubated at 37° C. throughout the entire period of organ culture in a rotating drum (speed of rotation 20 revolutions per hour).

The culture medium was Dulbecco's Modified Eagle's Medium (DMEM) made by MA Bioproducts, Walkersville, Md. L-glutamine was added to the medium in a concentration of 1.4%, together with 15% horse serum deactivated by heating. The horse serum (Gibco) was deactivated at 56° C. for 45 minutes. The complete medium was filtered through sterile filters (0.22 microns, Millipore).

After 24 hours the culture medium together with its various additives was changed and culture was then continued up to a total of 72 or a maximum of 96 hours.

The extent of bone resorption can be quantified by determining the calcium released into the medium. For this purpose, the calcium concentration in the culture medium was determined at time 0, 24, 48, 72 or 96 hours using a fluorescence titration method in a Corning 940 calcium analyser.

The results are the averages of 6 calvaries ± the mean error of the average. Statistically significant differences between the individual groups were determined by the t-test of Student. The significance was taken for a value $P<0.05$.

EXAMPLE 1

Effect of IFN-γ on Basal Bone Resorption

Figure 1:
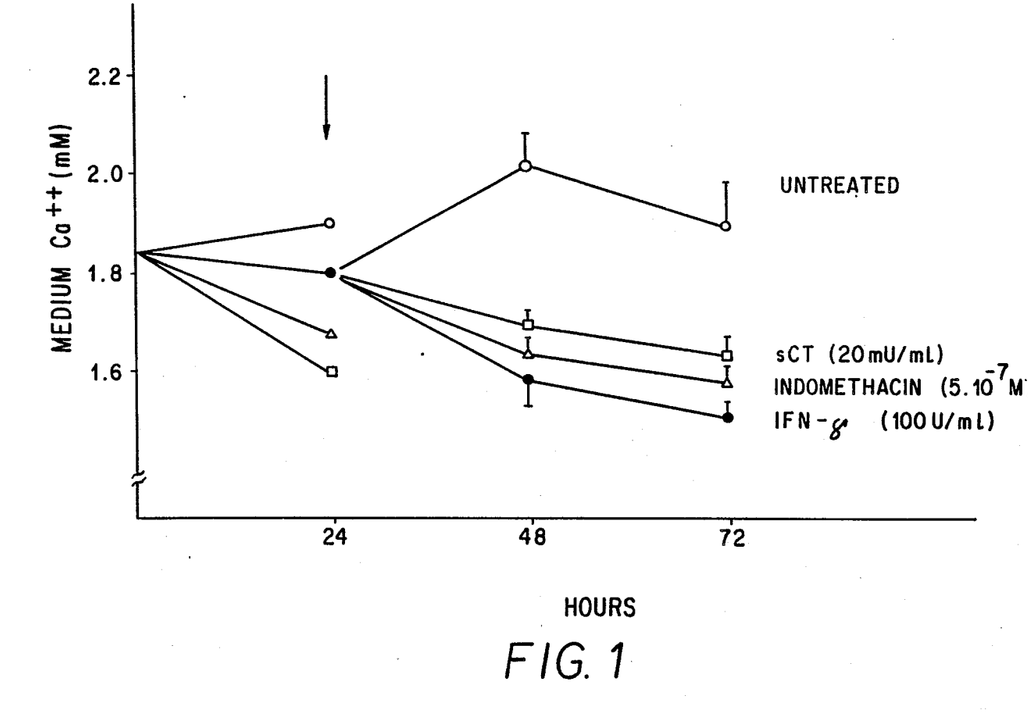
FIG. 1 shows the influence of IFN-γ on the calcium release from neonatal mouse calvaries (basal bone resorption).

If the bones were cultivated without any additives to the medium, a slight increase in the calcium concentration in the medium indicated that the bone was continuously resorbed (FIG. 1, controls). The reason for this is the endogenic formation of prostaglandins (Katz, et al., "The In Vitro Effect of Indomethacin on Basal Bone Resorption, on Prostaglandin Production and on the Response to Added Prostaglandins," *Prostaglandins*, 26:545 (1983) and Katz, et al., "Bone Resorption and Prostaglandin Production by Mouse Calvaria in Vitro: Response to Exogenous Prostaglandins and Their Precursor Fatty Acids," *Prostaglandins*, 22:537-543 (1981)). In fact, this basal resorption can be suppressed by the addition of indomethacin, a potent inhibitor of prostaglandin synthesis (J.R. Vane, "Inhibition of Prostaglandin-Synthesis as a Mechanism of Action for Aspirin-Like Drugs," *Nature*, 231:232 (1971)), as can be seen from FIG. 1.

The addition of IFN-γ to the culture medium in a concentration of 100 U/ml also brings about an inhibition of basal resorption which corresponds in its extent to the inhibiting effect of calcitonin and also the suppressant effect of indomethacin (see FIG. 1). The results are showing in the following Table 1.

TABLE 1

| | Medium $Ca^{++}$ in mmol/l (averages from 5 bones ± standard deviation) | | |
|---|---|---|---|
| Additive | 24 h | 48 h | 72 H |
| untreated | 1.90 ± 0.06 | 2.02 ± 0.07 | 1.86 + 0.09 |
| sCt (salmon calcitonin) (20 mU/ml) | 1.64 ± 0.02 | 1.70 ± 0.02 | 1.65 ± 0.03 |
| Indomethacin ($5 \times 10^{-7}$ M) | 1.63 ± 0.01 | 1.61 ± 0.02 | 1.55 ± 0.06 |

TABLE 1-continued

| Additive | Medium Ca++ in mmol/l (averages from 5 bones ± standard deviation) | | |
|---|---|---|---|
| | 24 h | 48 h | 72 H |
| IFN-γ (100 U/ml) | 1.80 ± 0.03 | 1.69 ± 0.02 | 1.52 ± 0.04 |

EXAMPLE 2

Effect of IFN-γ on Thrombin-Induced Resorption

To determine whether IFN-γ would inhibit the endogenic prostaglandin production in cultivated bones the following test was developed: from the observation that the addition of thrombin to the culture medium intensifies the bone resorption which is inhibited by indomethacin (Gustafson et al., "Thrombin, a Stimulator of Bone Resorption," *Bioscience Reports*, 3:255-261 (1983)), and thus clearly stimulates endogenous PG synthesis, the effect of different thrombine concentrations on the resorption of mouse calvaries during a culture time of 72 hours was investigated.

Figure 2:
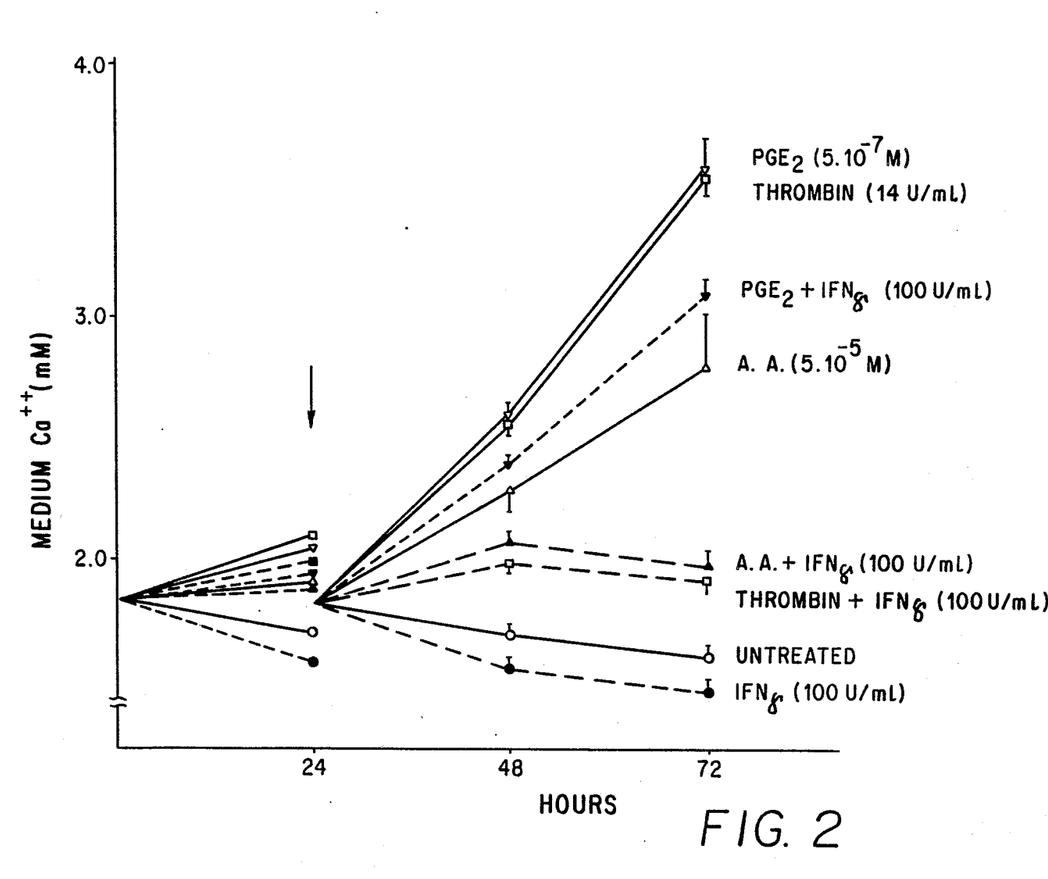
FIG. 2 shows the influence of IFN-γ on bone resorption, stimulated by PGE$_2$, thrombin or arachidonic acid (AA).
Figure 8:
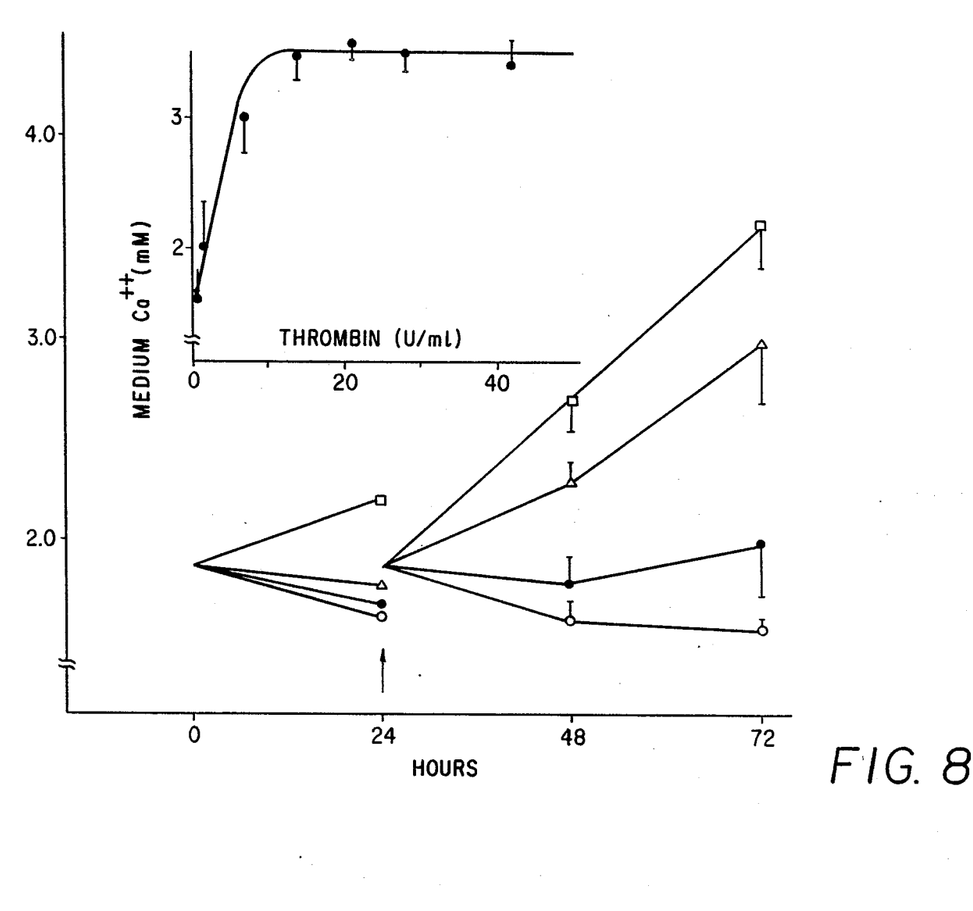
FIG. 8 describes a thrombine bioassay; the figure shows the passage of time and the dosage-activity curve of thrombine-induced bone resorption, 0, control; ●, 1U/ml; Δ, 7U/ml; □, 14 U/ml. The insert shows the dosage-activity curve of 0-42 U/.lm thrombin after 72 hours' culture time, measured by the calcium released into the culture medium.

Table 2 and FIG. 8 show that thrombin concentrations ranging from 14 to 42 units per ml of culture medium cause maximum release of calcium into the medium; the extent of stimulation of the resorption processes by thrombin shows only slight relative fluctuations within a test and, moreover, the absolute values of calcium release measured in a comparison of the individual tests were highly reproducible. This test is therefore well suited to determining the effect of the inhibitors of PG synthesis in the bone. The precise mechanism of activity of thrombin is not known, but it is believed that, due to its proteolytic activity (possibly through activating other proteases) it is able to activate a phospholipase which in turn cleaves arachidonic acid from membrane phospholipids. As a result, the substrate is continuously available for the cyclooxygenase system, so that the endogenic synthesis of various prostaglandins is subjected to constant stimulation. The following Table 2 and FIG. 2 show that IFN-γ completely suppresses the thrombin-induced bone resorption The effect of immuno-interferon is totally comparable with the effect of indomethacin ($5 \times 10^{-7}$ M).

TABLE 2

Thrombin Bioassay:

| Additive | Medium Ca++ in mmol/l (averages from 5 bones ± standard deviation) | | |
|---|---|---|---|
| | 24 h | 48 h | 72 h |
| Untreated | 1.66 ± 0.03 | 1.63 ± 0.07 | 1.61 ± 0.07 |
| Thrombin 1 U/ml | 1.67 ± 0.03 | 1.81 ± 0.09 | 2.01 ± 0.31 |
| Thrombin 7 U/ml | 1.81 ± 0.06 | 2.30 ± 0.11 | 3.02 ± 0.33 |
| Thrombin 14 U/ml | 2.13 ± 0.08 | 2.66 ± 0.11 | 3.56 ± 0.21 |
| Thrombin 21 U/ml | 2.21 ± 0.03 | 2.69 ± 0.05 | 3.63 ± 0.11 |
| Thrombin 28 U/ml | 2.28 ± 0.02 | 2.71 ± 0.06 | 3.61 ± 0.12 |
| Thrombin 42 U/ml | 2.30 ± 0.05 | 2.72 ± 0.10 | 3.52 ± 0.12 |

The 72 hour values were used in the insert for the dosage-activity curve.

| Additive | Medium Ca++ in mmol/l (averages from 5 bones ± standard deviation) | | |
|---|---|---|---|
| | 24 h | 48 h | 72 h |
| untreated | 1.72 ± 0.03 | 1.71 ± 0.02 | 1.63 ± 0.04 |
| IFN-γ(100 U/ml) | 1.60 ± 0.01 | 1.59 ± 0.02 | 1.52 ± 0.04 |
| PGE$_2$ ($5 \times 10^{-7}$ M) | 2.04 ± 0.03 | 2.60 ± 0.05 | 3.60 ± 0.13 |
| PGE$_2$ ($5 \times 10^{-7}$ M) + IFN-γ(100 U/ml) | 1.95 ± 0.04 | 2.40 ± 0.01 | 3.10 ± 0.06 |
| Thrombin (14 U/ml) | 2.11 ± 0.07 | 2.62 ± 0.05 | 3.62 ± 0.06 |
| Thrombin (14 U/ml) + IFN-γ(100 U/ml) | 1.99 ± 0.03 | 2.01 ± 0.04 | 1.92 ± 0.06 |
| Arachidonic acid ($5 \times 10^{-5}$ M) | 1.92 ± 0.05 | 2.35 ± 0.10 | 2.85 ± 0.27 |
| Arachidonic acid ($5 \times 10^{-5}$ M) + IFN-γ(100 U/ml) | 1.92 ± 0.09 | 2.01 ± 0.03 | 1.93 ± 0.03 |

EXAMPLE 3

Effect of IFN-γ on the PG-Synthetase Complex

To determine whether IFN-γ has an influence on the thrombin-initiated activation of other proteases or phospholipases or whether the immuno-interferon interacts directly with the prostaglandin synthetase complex. For this purpose, prostaglandin synthesis in the cultivated bone was stimulated by the addition of arachidonic acid to the culture medium. Katz et al., "Bone Resorption and Prostaglandin Production by Mouse Calvaria in Vitro: Response to Exogenous Prostaglandins and Their Precursor Fatty Acids," *Prostaglandins*, 22:537-543. (1981). This fatty acid is converted (as mentioned above) into various prostaglandins by the cyclooxygenase reaction. From its osteolytic activity (FIG. 2) it is clear that exogenic arachidonic acid is also used for prostaglandin synthesis in cultivated bones. IFN-γ can totally inhibit the bone resorption in the organ culture stimulated by arachidonic acid (FIG. 2). These tests show that IFN-γ can interface directly with the prostaglandin synthetase complex in the bone.

Figure 3:
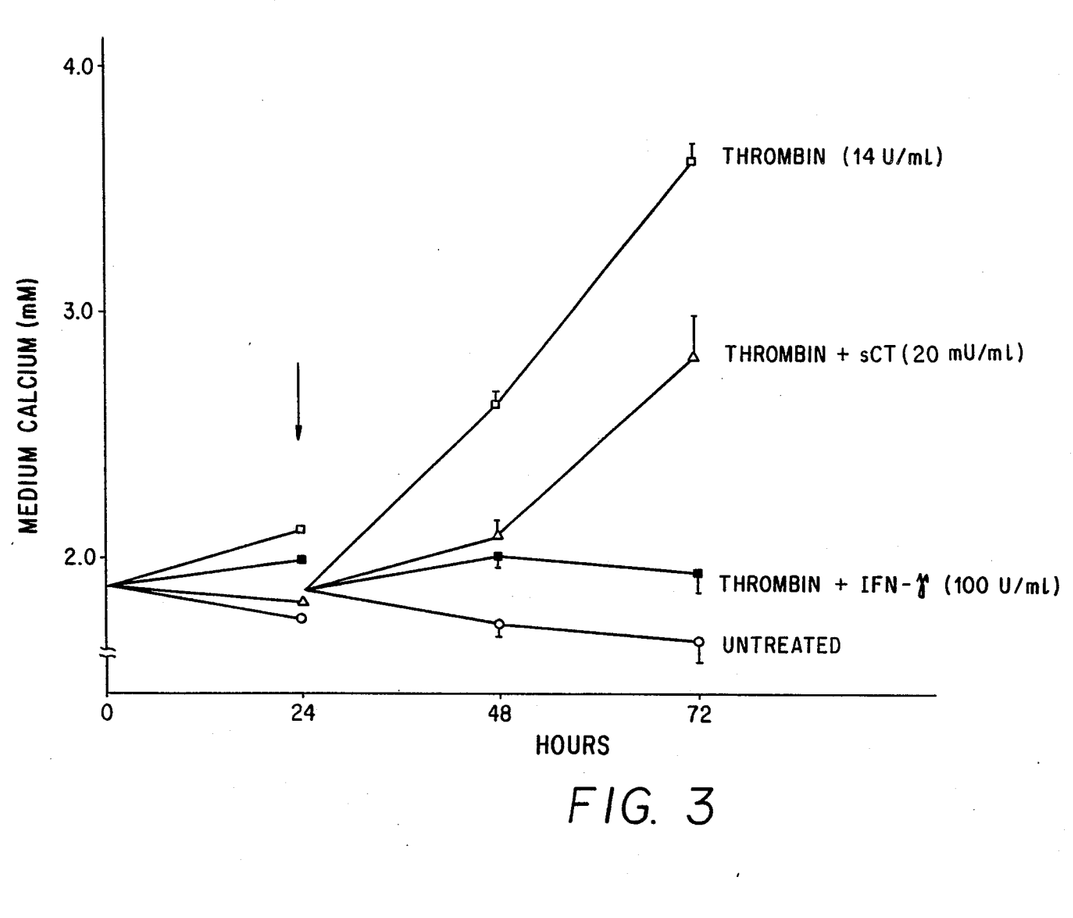
FIG. 3 shows the influence of salmon-calcitonin (SCT) on thrombine-induced resorption of cultivated neonatal mouse calvaries.
Figure 4:
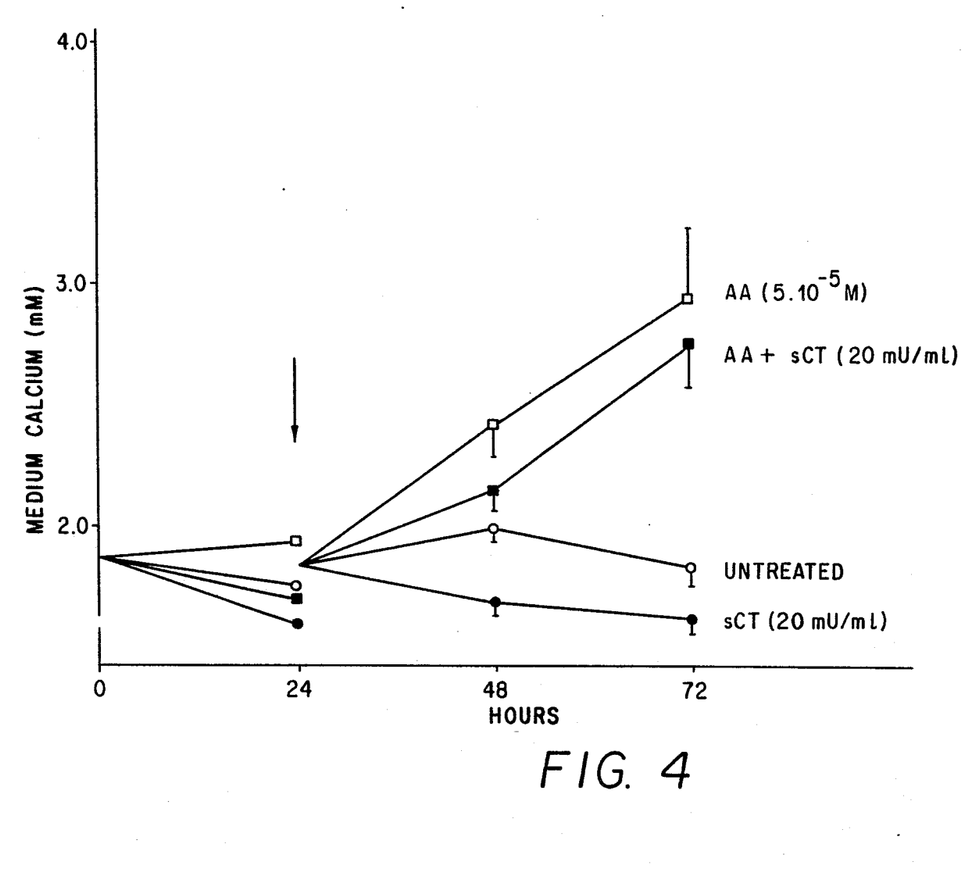
FIG. 4 shows the influence of salmon-calcitonin (SCT) on arachidonic acid (AA)-induced bone resorption.

In this context it should be emphasized that calcitonin has no significant influence either on thrombin-induced bone resorption or on arachidonic acid-induced bone resorption (see FIGS. 3 and 4 and Tables 3A and 3B).

TABLE 3A

| Additive | Medium Ca++ in mmol/l (averages from 5 bones ± standard deviation) | | |
|---|---|---|---|
| | 24 h | 48 h | 72 H |
| untreated | 1.74 ± 0.04 | 1.72 ± 0.05 | 1.64 ± 0.08 |
| Thrombin (14 U/ml) | 2.11 ± 0.07 | 2.62 ± 0.05 | 3.62 ± 0.06 |
| Thrombin + sCt (20 mU/ml) | 1.82 ± 0.01 | 2.08 ± 0.08 | 2.82 ± 0.19 |
| Thrombin (14 U/ml) + IFN-γ(100 U/ml) | 1.93 ± 0.03 | 2.01 ± 0.04 | 1.92 ± 0.06 |

TABLE 3B

| Additive | Medium Ca++ in mmol/l (averages from 5 bones ± standard deviation) | | |
|---|---|---|---|
| | 24 h | 48 h | 72 H |
| untreated | 1.78 ± 0.03 | 2.01 ± 0.04 | 1.85 ± 0.06 |
| AA ($5 \times 10^{-5}$ M) | 1.95 ± 0.03 | 2.41 ± 0.11 | 2.96 ± 0.28 |
| AA ($5 \times 10^{-5}$ M) + sCt (20 mU/ml) | 1.72 ± 0.02 | 2.13 ± 0.05 | 2.78 ± 0.20 |
| sCt (20 mU/ml) | 1.64 ± 0.02 | 2.18 ± 0.06 | 1.65 ± 0.03 |

EXAMPLE 4

Influence of IFN-γ on Resorption Stimulate by PGE$_2$ and PTH

Figure 5:
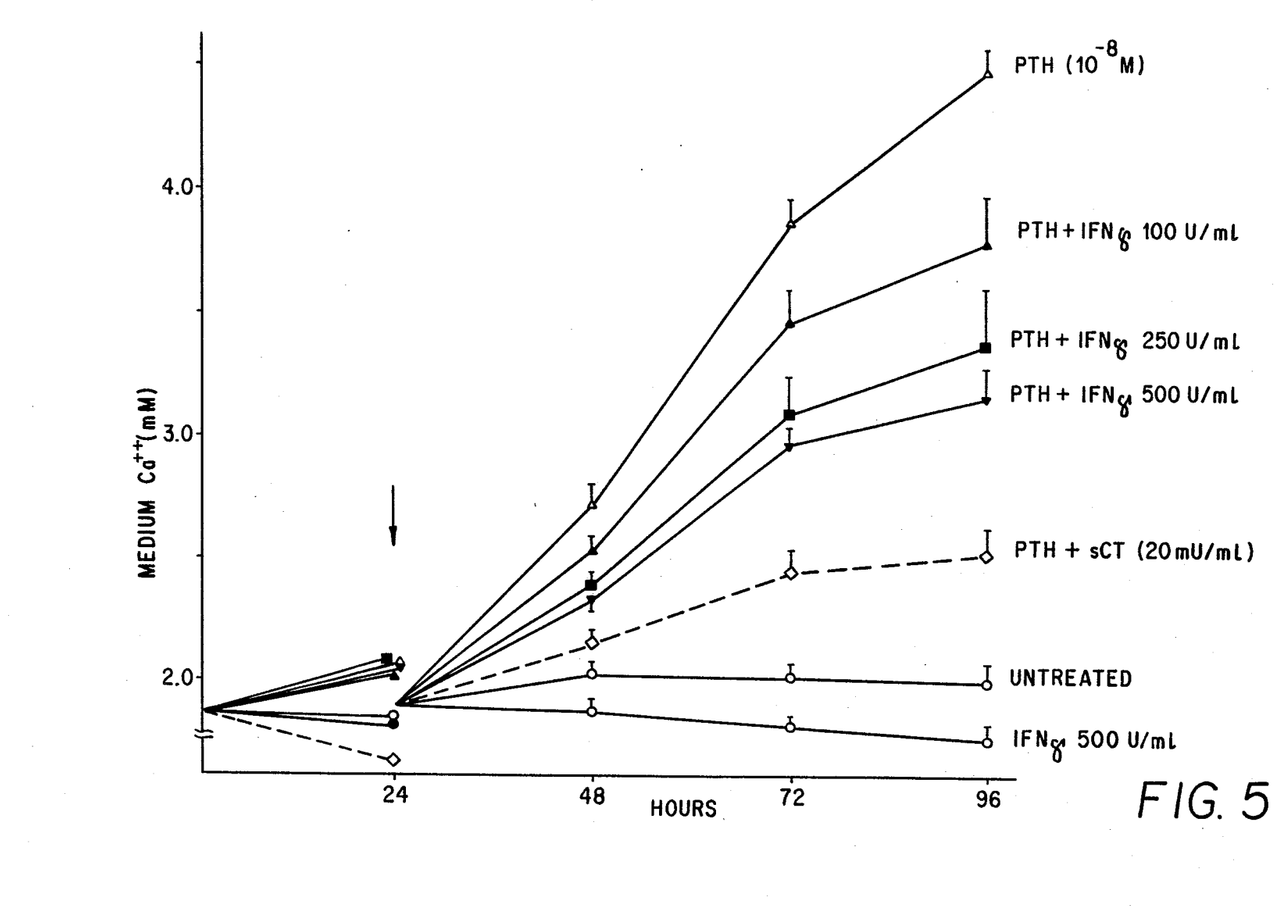
FIG. 5 shows the calcitonin-like effect on IFN-γ on parathormone (PTH)-induced bone resorption of cultivated neonatal mouse calvaries.

Once it was established that IFN-γ suppressed prostaglandin synthesis, it was expected that its influence on the osteolytic activity of PGE$_2$ which had been added to the culture medium would tend to be slight. In fact, et al., "Effects of Parathyroid Hormone and Calcitonin on Osteoclast Formation in Vitro," *Endocrinology*, 107:1137–1143 (1980). The test results shown in Table 4 and in FIG. 5 indicate that IFN-γ has, in addition to its effect on prostaglandin synthesis, a calcitonin-like effect on PTH-induced bone resorption. The effect of 20 mU/ml of salmon calcitonin on PTH activity is also shown for comparison purposes.

TABLE 4

| Additive | Medium Ca$^{++}$ in mmol/l (averages from 5 bones ± standard deviation) | | | |
|---|---|---|---|---|
| | 24 h | 48 h | 72 H | 96 h |
| untreated | 1.85 ± 0.02 | 2.04 ± 0.04 | 2.06 ± 0.06 | 2.03 ± 0.06 |
| IFN-γ (500 U/ml) | 1.89 ± 0.03 | 1.89 ± 0.04 | 1.84 ± 0.03 | 1.78 ± 0.03 |
| PTH (10$^{-8}$ M) | 2.08 ± 0.05 | 2.75 ± 0.07 | 3.89 ± 0.06 | 4.51 ± 0.06 |
| PTH (10$^{-8}$ M) + IFN-γ(100 U/ml) | 2.07 ± 0.02 | 2.55 ± 0.06 | 3.49 ± 0.11 | 3.82 ± 0.17 |
| PTH (10$^{-8}$ M) + IFN-γ(250 U/ml) | 2.05 ± 0.04 | 2.39 ± 0.07 | 3.12 ± 0.16 | 3.40 ± 0.25 |
| PTH (10$^{-8}$ M) + IFNγ(500 U/ml) | 2.08 ± 0.05 | 2.36 ± 0.01 | 2.99 ± 0.05 | 3.19 ± 0.09 |
| PTH (10$^{-8}$ M) + sCt(20 mU/ml) | 1.65 ± 0.01 | 2.15 ± 0.05 | 2.45 ± 0.10 | 2.52 ± 0.13 |

FIG. 2 shows that IFN-γ has only a slight influence on the osteolytic activity of PGE$_2$. However, it was striking that this inhibitory effect was greater than the corresponding suppression of the basal bone resorption brought about by endogenic prostaglandin synthesis. An investigation was carried out to see whether IFN-γ, in addition to inhibiting prostaglandin synthesis, might not also influence the consequent effects of prostaglandins. There included, in particular the activation of osteoclasts. Gustafson et al., "Thrombin, A Stimulator of Bone Resorption," *Bioscience Reports*, 3:255–261 (1983).

Parathormone also leads to an increase in the number and activity of osteoclasts in organ culture, although in a way which is independent of prostaglandins. Feldman

EXAMPLE 5

Influence of IFN-γ, on Basal and Stimulated Resorption

Figure 6:
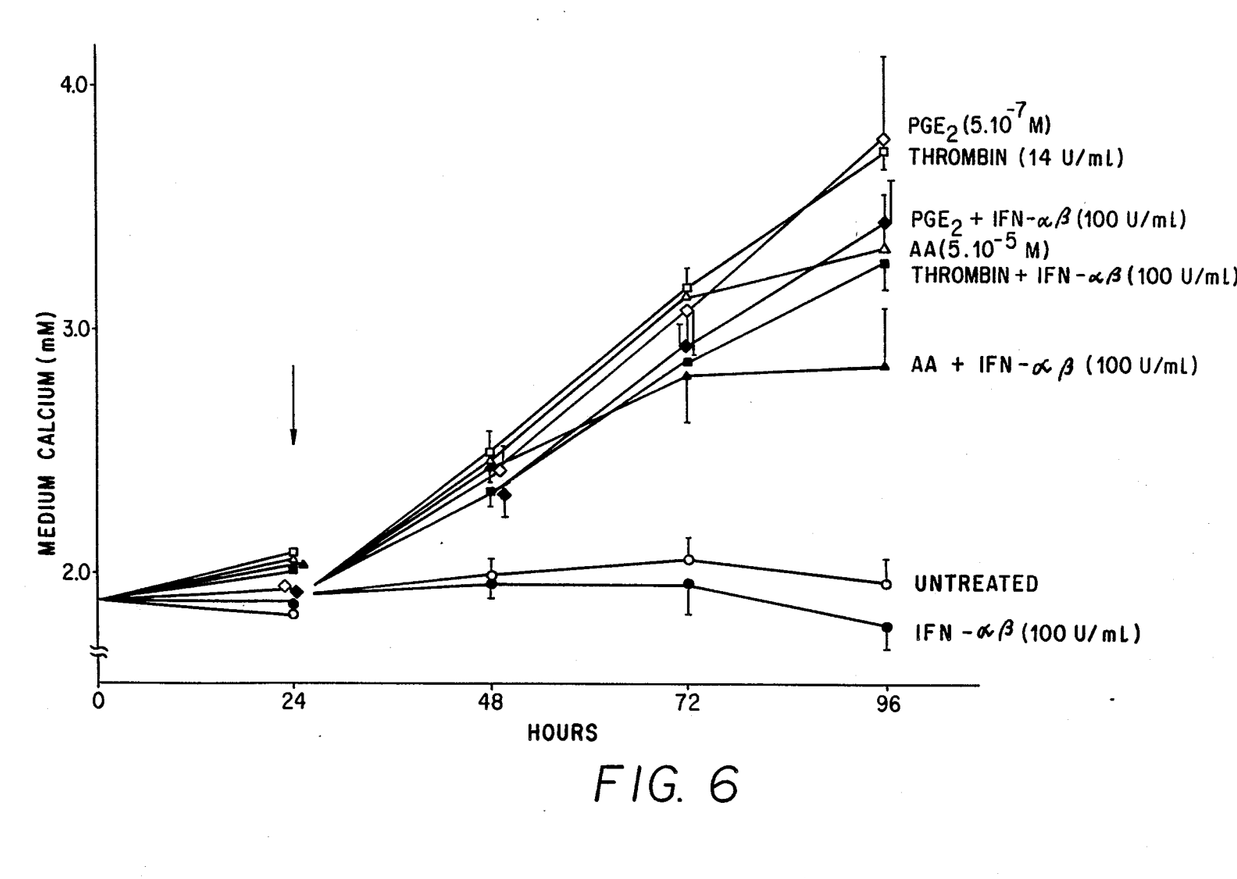
FIG. 6 shows the influence of IFN-α,β on bone resorption of cultivated neonatal mouse calvaries.
Figure 7:
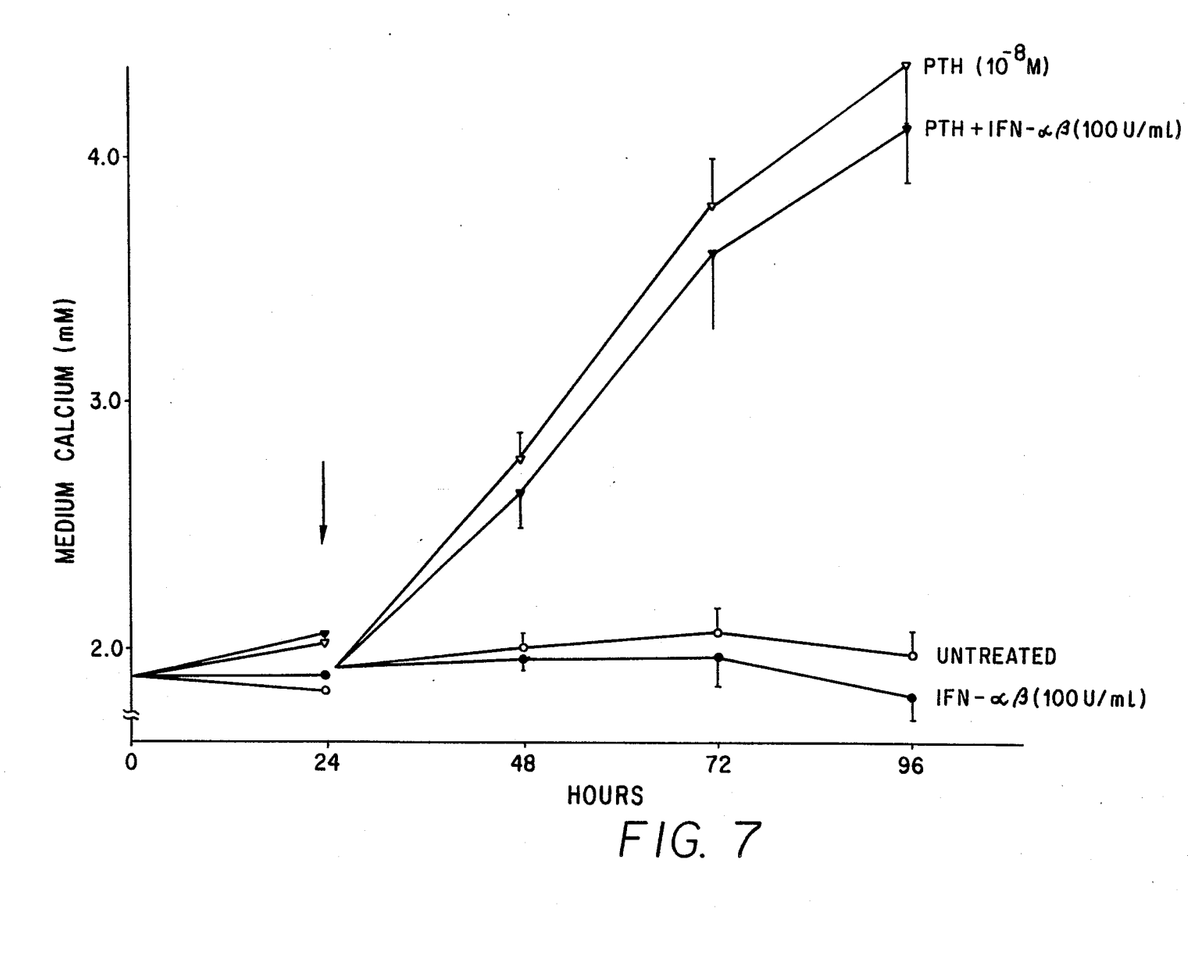
FIG. 7 shows the IFN-α,β and parathormone (PTH) induction of bone resorption of cultivated neonatal mouse calvaries.

In order to establish whether the effect on prostaglandin synthesis, in particular, is specific to IFN-γ or is also exerted by other types of interferon, the test series was repeated with an α,β-interferon (IFN-α,β). FIG. 6 shows that this type of interferon, unlike IFN-γ, cannot bring about any noticeable inhibition of the bone resorption induced by thrombin or arachidonic acid. In the concentration used (100 U/ml of medium) no inhibition of the PTH-induced bone resorption by IFN-γ, could be detected either (FIG. 7). The results are shown in the Tables 5A and 5B which follow.

TABLE 5A

| Additive | Medium Ca$^{++}$ in mmol/l (averages from 5 bones ± standard deviation) | | | |
|---|---|---|---|---|
| | 24 h | 48 h | 72 H | 96 h |
| untreated | 1.85 ± 0.03 | 2.02 ± 0.04 | 2.09 ± 0.08 | 2.01 ± 0.08 |
| IFNα/β (100 U/ml) | 1.88 ± 0.08 | 2.02 ± 0.10 | 1.98 ± 0.12 | 1.92 ± 0.12 |
| PGE$_2$ (5 × 10$^{-7}$M) | 1.98 ± 0.05 | 2.44 ± 0.08 | 3.13 ± 0.19 | 3.91 ± 0.25 |
| PGE$_2$ (5 × 10$^{-7}$M) + IFNα/β (100 U/ml) | 1.96 ± 0.05 | 2.38 ± 0.06 | 2.96 ± 0.11 | 3.49 ± 0.16 |
| Thrombin (14 U/ml) | 2.08 ± 0.04 | 2.50 ± 0.01 | 3.20 ± 0.06 | 3.81 ± 0.08 |
| Thrombin (14 U/ml) + IFNα/β (100 U/ml) | 2.04 ± 0.02 | 2.36 ± 0.02 | 2.89 ± 0.07 | 3.31 ± 0.13 |
| AA. (5 × 10$^{-7}$M) | 2.07 ± 0.03 | 2.50 ± 0.08 | 3.15 ± 0.16 | 3.39 ± 0.27 |
| AA. (5 × 10$^{-7}$M) + IFNα/β (100 U/ml) | 2.03 ± 0.04 | 2.46 ± 0.07 | 2.84 ± 0.11 | 2.89 ± 0.22 |

TABLE 5B

| Additive | Medium Ca$^{++}$ in mmol/l (averages from 5 bones ± standard deviation) | | | |
|---|---|---|---|---|
| | 24 h | 48 h | 72 H | 96 h |
| untreated IFNα/β | 1.85 ± 0.03 | 2.02 ± 0.04 | 2.09 ± 0.08 | 2.01 ± 0.08 |

TABLE 5B-continued

| | Medium Ca$^{++}$ in mmol/l (averages from 5 bones ± standard deviation) | | | |
|---|---|---|---|---|
| Additive | 24 h | 48 h | 72 H | 96 h |
| (100 U/ml) | 1.88 ± 0.08 | 2.02 ± 0.10 | 1.98 ± 0.12 | 1.92 ± 0.12 |
| PTH (10$^{-8}$M) | 2.04 ± 0.04 | 2.78 ± 0.09 | 3.91 ± 0.22 | 4.42 ± 0.39 |
| PTH (10$^{-8}$M) + IFNα/β (100 U/ml) | 1.97 ± 0.06 | 2.64 ± 0.11 | 3.62 ± 0.23 | 4.14 ± 0.27 |

Having now fully described this invention, it will become readily apparent to one with ordinary skill in the art that many changes and modifications may be made thereto without affecting the spirit or scope thereof.

What is claimed is:

1. A method for inhibiting, preventing, or controlling bone loss in a patient comprising administering a pharmaceutical composition to said patient comprising gamma-interferon in an amount effective to inhibit, prevent, or control said bone loss.

2. The method of claim 1 wherein said bone loss is a degenerative systemic or local bone loss of inflammatory or non-inflammatory origin.

3. The method of claim 1 wherein said bone loss is caused by local or generalized decomposition of the bone tissue.

4. The method of claim 1 wherein said bone loss is caused by pathological disease.

5. The method of claim 1 wherein said bone loss is a result of osteoporosis.

6. The method of claim 1 wherein said bone loss is a result of Paget's disease.

7. The method of claim 1 wherein said bone loss is the result of rheumatic arthritis.

8. The method, of claim 1 wherein said bone loss is the result of jaw and tooth diseases.

9. The method of claim 1 wherein said bone loss is the result of osteodystophies caused by parathormone.

10. The method of claim 1 wherein said bone loss is the result of hypercalcaemia in prostaglandinsynthesizing tumors.

11. A method for inhibiting, preventing, or controlling bone loss is a patient comprising adminstering a pharmaceutical composition to said patient comprising gamma-interferon in an amount effective to inhibit, prevent, or control bone loss, in combination with calcitonin in an amount sufficient to inhibit, prevent, or control bone loss.

* * * * *

UNITED STATES PATENT AND TRADEMARK OFFICE
CERTIFICATE OF CORRECTION

PATENT NO. : 4,921,697

DATED : May 1, 1990

INVENTOR(S) : Meinrad Peterlik, et al.

It is certified that error appears in the above-identified patent and that said Letters Patent is hereby corrected as shown below:

In column 2, line 34, delete "bore" and replace therein --bone--.

Column 4, lines 37-61 should be all one paragraph;
  in line 56, "Res., 4" should be italicized;
  in line 57, delete "obtain" and replace therein --obtained--.

In column 5, line 32, delete "difference" and replace therein-- different--.

Column 6, line 62 should start a new paragraph.

In column 7, line 40, delete the first period ".".

In column 7, line 60, delete th period ".".

In column 8, line 64, delete "+0.09" and replace therein --$\pm$0.09--.

In column 11, line 34, delete "There" and replace therein --These--.

UNITED STATES PATENT AND TRADEMARK OFFICE
CERTIFICATE OF CORRECTION

PATENT NO. : 4,921,697

DATED : May 1, 1990

INVENTOR(S) : Meinrad Peterlik, et al.

It is certified that error appears in the above-identified patent and that said Letters Patent is hereby corrected as shown below:

In claim 11, line 2, delete "is" and replace therein --in--.

Signed and Sealed this

Twenty-fourth Day of December, 1991

*Attest:*

HARRY F. MANBECK, JR.

*Attesting Officer*      *Commissioner of Patents and Trademarks*